United States Patent [19]
Schubert et al.

[11] Patent Number: 5,840,513
[45] Date of Patent: Nov. 24, 1998

[54] ANTIBODIES DIRECTED TO PAGC PEPTIDES FOR THE DETECTION OF SALMONELLAE

[75] Inventors: Peter Schubert, Darmstadt; Siegfried Neumann, Seeheim-Jugenheim; Christa Burger, Darmstadt; Winfried Linxweiler, GroB-Umstadt; Andreas Bubert, Gerbrunn; Werner Goebel, Veitschochheim; Hans-Joachim Mollenkopf, Randersacker, all of Germany

[73] Assignee: Merck Patent Gesellschaft mit Beschrankter Haftung, Germany

[21] Appl. No.: 372,197

[22] Filed: Jan. 13, 1995

[30] Foreign Application Priority Data

Jan. 14, 1994 [DE] Germany .................. 44 00 990.9

[51] Int. Cl.$^6$ .................. G01N 33/569; C07K 16/12
[52] U.S. Cl. .................. 435/7.35; 530/327; 530/387.9; 530/388.2; 530/388.4; 530/389.5; 530/391.3; 530/391.7; 424/139.1; 424/150.1; 424/164.1
[58] Field of Search .................. 530/387.9, 327, 530/388.2, 389.5, 388.4, 391.3, 391.7; 435/7.35; 424/139.1, 150.1, 164.1

[56] References Cited

U.S. PATENT DOCUMENTS 5,415,997  5/1995  Atrache et al. .................. 435/7.35

FOREIGN PATENT DOCUMENTS 9217785  10/1992  WIPO .................. 435/7.35

OTHER PUBLICATIONS

G.B. Wisdom, "Enzyme–Immunoassay," *Clinical Chemistry* vol. 22/8, 1976, pp. 1243–1255.

*Bergey's Manual of Systematic Bacteriology,* vol. 1, Edited by Noel Krieg, Published By Williams & Wilkens, 1984, Table 5.2, pp. 412–413.

*Primary Examiner*—Anthony C. Caputa
*Attorney, Agent, or Firm*—Millen, White, Zelano & Branigan, P.C.

[57] ABSTRACT

The invention relates to agents and methods for the immunological detection of bacteria of the genus Salmonella. The agents according to the invention include peptides whose sequence is selected from the PagC protein, and which are suitable for producing specific antibodies for the immunological detection of salmonellae.

9 Claims, 2 Drawing Sheets

ANTIBODIES DIRECTED TO PAGC PEPTIDES FOR THE DETECTION OF SALMONELLAE

BACKGROUND OF THE INVENTION

The invention relates to agents and methods for the immunological detection of bacteria of the genus Salmonella, and also selected peptides from the external membrane protein PagC.

The pathogens of the genus Salmonella are gram-negative, usually flagellate rods, which can grow both aerobically and optionally anaerobically without great demand on the nutrient medium. The high environmental resistance of these widespread bacteria is of great epidemiological importance. Survival times of several weeks to months were thus found, even at low temperatures, e.g., in foodstuffs, household dust, tap water, stagnant water and garden soil. Fundamentally, two different types of illness caused by salmonellae are differentiated:

1. General typhoid infection (typhus, paratyphus), caused by Salmonella typhi and S. paratyphi. Usually transmission takes place by the faecal/oral route or by means of contaminated foodstuffs. 2. Acute gastroenteritis (salmonelloses), caused by over 200 different Salmonella serotypes. Transmission essentially takes place by means of contaminated foodstuffs.

The severity of a salmonellosis, which is manifested after oral assimilation of the bacteria after about 24 hours mainly by vomiting and diarrhoea, is dependent on the serotype and on the infectious dose. In addition, the age and the immune status also play a part. Within the Enterobacteriaceae family, salmonellae in addition to E. coli and Shigella species are the most frequent causes of food poisoning. A rapid rise in salmonelloses has been recorded in the last few years. Between 1985 and 1 991, the number of reported cases in Germany has nearly quadrupled from 30,000 to 114,000. The cause is regarded to a large extent as being large-scale animal keeping, especially that of chickens, and inadequate hygiene in the processing of animal products, as well as a lack of hygiene consciousness in large and domestic kitchens. Transmission mainly takes place through meat products, eggs, milk products and baked goods.

In the area of foodstuffs control, but also in medicine, there is therefore an increasing need for rapid and safe methods for the detection of salmonellae. Officially prescribed detection methods are based on operations in which the bacteria are cultured on three different nutrient media:

1. Non-selective enrichment.
2. Selective enrichment.
3. Growth on solid selective nutrient media with subsequent serotyping. Altogether, this process lasts 4–5 days.

A prerequisite for a quick and specific treatment of the ill and for the rapid checking of the source of infection are quick and specific methods for the detection of salmonellae. Official regulations for the detection of salmonellae demand that the methods used for these bacteria must be sensitive, independently of pathogenicity and virulence. To shorten the long detection times of the official method, molecular genetic and immunological methods are primarily suitable.

In general, the use of nucleic acid probes is not so sensitive that a preculture can be dispensed with. For this reason, the colony hybridization method is a customary, but labor-intensive process variant. Detection methods which are based on the amplification of nucleic acid regions, e.g., the polymerase chain reaction in general improve the detection limit, but could be inhibited by various substances present, e.g., in foodstuffs (Wernars et al. 1991. *J. Appl. Bacteriol.* 70: 121–126).

Immunological detection methods have proven suitable in routine diagnosis, but in the literature few antibodies have been described to date which are capable of detecting salmonellae. The classical antigens for the development of salmonellae-specific antibodies are based either on somatic (O-antigen) factors, e.g. a specific part of the bacterial lipopolysaccharide layer (EP 0 494 085) or on flagellae (H)-antigens (WO 86/00-993, WO 86/04-352 and WO 89/01-162). Moreover, certain surface (Vi)-antigens are used. In this case, they are receptors for bacteriophages (Ackerman, H.-W., Dubow, M. S.–*Viruses of Prokaryotes.* 2 volumes. CRC Press, Boca Raton, 1987).

In the WHITE-KAUFMANN-LE MINOR scheme for the identification and classification of salmonellae, all three antigen factors (O, H, Vi) mentioned are taken into account. With over 2200 different serotypes at present, inevitable shortcomings of screening tests result with antibodies which are directed against these antigen factors. To minimize the detection problems, antibody mixtures directed against various of these antigen factors are frequently employed. This procedure, however, is very time- and cost-intensive.

In WO 92/17 785 the use of antibodies which are directed against PagC is proposed for the immunological detection of salmonellae. This antigen, PagC from Salmonella, having a molecular weight of about 18 kilodaltons is a protein which is localized in the external membrane of these bacteria. Salmonellae having a PagC mutation are avirulent, as they are not capable of survival in host cells. It was also possible to detect the gene coding for PagC in other Salmonella species and it is obviously present in all salmonellae (Pulkkinen and Miller, 1991, *J. Bacteriol.* 173: 86–93). The expression of PagC is non-constitutive, but is under the control of the so-called two-component system PhoP/PhoQ. PhoQ is in this case a sensor protein which reacts to external environmental influences and transmits this information to the transmitter protein PhoP. The activated PhoP in turn is able to stimulate the transcription of the pagC gene.

The expression of PagC can be amplified, e.g., by pH decrease in the medium, phosphate limitation thereof or alternatively by a stationary growth phase.

The expression of PagC or similar proteins, however, is not restricted to Salmonella. It was also possible to identify PagC-homologous proteins in other Enterobacteriaceae, (OmpX from Enterobacter cloacae, Ail from Yersinia enterocolitica, Lom from E. coli carrying lambda phages). For this reason, polyclonal antibodies which were obtained by immunization against the total PagC are not suitable for the specific detection of salmonellae. In WO 92/17 785 the use of the peptide Arg Gly Val Asn Val Lys Arg Tyr Glu Asp Asp Ser Phe (RGVNVKYRYEDDSF; (SEQ ID NO:8) from PagC is furthermore proposed as an immunogen for the production of polyclonal antibodies. However, because of the pronounced sequence homology to the PagC-like proteins from other enterobacteria, the resulting antibodies are also unsuitable for the specific detection of salmonellae.

SUMMARY OF THE INVENTION

It is an object of the present invention to make available improved agents and methods for the immunological detection of bacteria of the genus Salmonella. In particular, peptides according to the invention for the specific production of specific antibodies which are suitable for the immunological detection of salmonellae are made available.

The invention relates to peptides selected from the protein PagC, having a sequence according to one of the formulae Ia to Ie (SEQ ID NO:1 to SEQ ID NO:5).

Glu Pro Glu Gly Ile His Tyr His Asp Lys Phe Glu Val    Ia (SEQ ID NO:1)

Ala Thr Phe Lys Glu His Ser Thr Gln Asp Gly Asp Ser    Ib (SEQ ID NO:2)

Gly Asp Arg Ala Ser Gly Ser Val Glu Pro Glu Gly    Ic (SEQ ID NO:3)

Gln Ser Lys Val Gln Asp Phe Lys Asn Ile Arg    Id (SEQ ID NO:4)

Glu His Ser Thr Gln Asp Gly Asp Ser Phe Ser Asn Lys    Ie (SEQ ID NO:5)

The invention also relates to the use of one of the peptides mentioned having a sequence according to one of the formulae Ia to Ie (SEQ ID NO:1 to SEQ ID NO:5) for the production of immunogenic conjugates. The peptide can be conjugated to a carrier, as described below; the peptide conjugated to the carrier can be used to elicit an immune response, hence an immunogenic conjugate.

The invention also relates to an antibody which is specifically directed against an epitope which is formed from a peptide according to one of the formulae Ia–Ie (SEQ ID NO:1 to SEQ ID NO:5). The antibody can be conjugated to a detectable label, i.e., a marker or reporter molecule, such as an enzyme, fluorochrome or biotin.

The invention furthermore relates to the use of an antibody which is directed against one of the epitopes having an amino acid sequence according to one of the formulae Ia–Ie (SEQ ID NO:1 to SEQ ID NO:5) for the detection of bacteria of the genus Salmonella.

The invention also relates to methods for the detection of bacteria of the genus Salmonella by means of an antibody which is directed against one of the epitopes having an amino acid sequence according to one of the formulae Ia–Ie (SEQ ID NO:1 to SEQ ID NO:5).

The invention further relates to test compositions for the immunological detection of bacteria of the genus Salmonella, which contain an antibody against an epitope according to one of the formulae Ia–Ie (SEQ ID NO:1 to SEQ ID NO:5).

A test composition or kit can also contain the antibody conjugated to a detectable label, e.g,. an enzyme such as alkaline phosphatase; a microtiter well coated with an antibody which binds the antibody directed to an epitope of 1a–1e or a variant thereof; substrate solutions for detecting the label, e.g,. the enzyme; rinsing solutions; controls, positive and negative, e.g., extracts of Salmonella and E. coli, E. cloacae, P. mivabilis or C. freundi, respectively. Alternatively, the label can be conjugated to a second antibody which reacts with the antibody according to the present invention, e.g., if the first antibody is mouse, then the second could be goat anti-mouse, and used according to conventional ELISA assays.

Upon further study of the specification and appended claims, further objects and advantages of this invention will become apparent to those skilled in the art.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

The invention is described in greater detail in the following. Details of biochemical, immunological and molecular biological methods which are known to the person skilled in the art, and whose details are described in the literature, are not gone into in greater detail. In these methods, use can also be made of variants which are known per se and not described here in greater detail.

The peptides according to the invention of the formulae Ia–Ie (SEQ ID NO:1 to SEQ ID NO:5) can be used as immunogenic peptides for the production of antibodies and thus make possible specific immunological detection of bacteria of the genus Salmonella.

It is known to the person skilled in the art that the replacement of one or a few amino acids in a peptide frequently does not change its biological properties. Because of this the peptide sequences according to the invention also include those which are derived from the sequences Ia–Ie (SEQ ID NO:1 to SEQ ID NO:5) by amino acid replacement, and which biologically show the same action as the respective peptides having the original sequence, eg., eliciting an antibody having an equipotent or improved immunological specificity for PagC. Indications of the possibility of amino acid replacements of this type are taken by the person skilled in the art, for example, from the compilation of Dayhoff, M. O. in *Atlas of Protein Sequence and Structure*, Vol. 5, page 98 (1972). In a similar manner, the removal of one or a few amino acids on one or both ends of the peptide frequently has no or little effect on the immunogenicity of the resulting immunogenic conjugates or on the specificity of the resulting antibodies. The same also applies if one or a few amino acids are added to one or both ends of the peptide. Because of this, these variants of the peptides according to the invention and the antibodies produced with their aid are additionally included by the invention. The ability of a peptide variant to elicit an immune response can be determined as described according to the present invention, e.g., in Examples 3–5.

Based on the amino acid sequence, the peptides can be synthesized by processes known to the person skilled in the art, for example the t-boc or the fmoc process (tert-butoxycarbonylor9-fluorenylmethyloxycarbonyl). Details of these processes are described, for example, in *J. Am. Chem. Soc.* 85, 2149–2154 (1963) and in *Synthetic Polypeptides as Antigens* (van Regenmortel et al. (eds.) Elsevier 1988 (Volume 19 of the series Laboratory Techniques in Biochemistry and Molecular Biology). The fmoc process, in particular mechanized process variants, is preferred. Details of the process as well as suitable amino acid protective groups are known to the person skilled in the art.

In general, peptides are unsuitable for producing antibodies. However, if peptides are coupled to high molecular weight carrier substances, immunogenic conjugates are formed. The peptides according to the invention can be conjugated with known carrier substances. These include polyethylene glycols, serum albumins, KLH (keyhole limpet haemocyanin), ovalbumin, glucose dehydrogenase from Bacillus megatherium and PPD (purified protein derivative of tuberculin).

Preferred carrier substances are KLH and glucose dehydrogenase from B. megatherium.

Bridge compounds (linkers) are often additionally employed in the synthesis of the conjugates. These are low molecular weight organic compounds having at least two bridgeable functional groups. Suitable compounds are known to the person skilled in the art; these include, for example: 1,2-diaminoethane, succinic acid, β-alanine, 1,6-diaminohexane, 6-aminocaproic acid, adipic acid and cysteine. Cysteine is preferably employed as a linker, this amino acid radical already being incorporated in the synthesis of the peptide. m-Maleimidobenzoyl-N-hydroxysuccinimidester (MBS) is preferably employed for producing the bonds between peptide and carrier substance.

The immunogenic conjugates mentioned are used to produce antibodies in test animals by known processes. Mammals, for example sheep, goats, rabbits or mice, are customarily used for this purpose. Rabbits are preferred for the production of polyclonal antibodies. However, it is also possible to produce monoclonal antibodies with the aid of the immunogenic conjugates according to the invention. Details of the immunological methods are known to the person skilled in the art. Information on carrying out these processes is additionally to be found frequently in the literature; the following may be mentioned for example:

*Antibodies*, E. Harlow and D. Lane, Cold Spring Harbor (1988)

Woodard, L. F. and Jasman, R. L. (1985) *Vaccine* 3, 137–144

Woodard, L. F. (1989) *Laboratory Animal Sci* 39, 222–225

*Handbook of Experimental Immunology* (1986) Weir, D. M. et al. eds.; Blackwell Scientific Publications, Oxford, GB These processes include, for example, the conjugation and immunization process, and also the production and purification of antibodies and immunological detection methods. The immunological detection methods in which antibodies according to the invention can be used preferably include agglutination methods, immunometric detection methods, the immunoblot method and in particular the sandwich (ELISA) method.

According to the invention, the term antibody includes both immunoglobulins and antisera. It is furthermore known to the person skilled in the art that in methods of this type, instead of the use of a single antibody which is directed against a single epitope, a mixture of various antibodies of various specificity produces advantages, in particular with respect to the detection sensitivity. This is particularly true of monoclonal antibodies, but also of other antibodies which are directed against one epitope in each case. Correspondingly, it may be advantageous to combine several antibodies which are directed against various peptide structures according to the formulae Ia–Ie (SEQ ID NO:1 to SEQ ID NO:5) for the use according to the invention and/or the methods according to the invention.

By "isolated", it is meant that the antibody or peptide is in a form other than found in nature, e.g., more concentrated, more purified, and/or separated from other blood components.

Details of the preparation of the peptides according to the invention, and also their use are evident from the following examples. The person skilled in the art takes further methodological details from the cited literature. The examples are intended to illustrate the subject of the invention and not to restrict the invention.

Without further elaboration, it is believed that one skilled in the art can, using the preceding description, utilize the present invention to its fullest extent. The preferred specific embodiments are, therefore, to construed as merely illustrative, and not limitative of the disclosure in any way whatsoever.

The entire disclosures of all applications, patents, and publications cited above and below, and of corresponding application German P 44 00 990, filed Jan. 14, 1994, are hereby incorporated by reference.

EXAMPLES

Example 1

Chemical synthesis of the peptide CysGluHisSerThrGlnAspGlyAspSerPheSerAsnLys (SEQ ID NO:6)

The fmoc method (9-fluoroenylmethyloxycarbonyl protective group) is used for the chemical synthesis of the peptide CysGluHisSerThrGlnAspGlyAspSerPheSerAsnLys (SEQ ID NO:6). This peptide corresponds to a peptide of the formula Ie (SEQ ID NO:5) having an additional N-terminal cysteine residue as a linker. A peptide synthesizer from Applied Bio-systems is used for the synthesis; the process parameters are contained in the apparatus documentation.

A polymeric carrier containing 4-(2',4'-dimethoxyphenylaminomethyl)phenoxy groups is used as the solid phase. The amino acids are employed as α-N-fmoc derivatives. If the amino acids contain reactive side chains, these are masked by additional protective groups which can be removed by trifluoroacetic acid hydrolysis. The peptide bonds are produced by activation of the carboxyl groups by means of diisopropylcarbodiimide. The sequence of the amino acid derivatives employed follows from the desired sequence. In the first step of the synthesis cycle, the amino group on the solid phase reacts, i.e. in the first cycle the amino groups of the 4-(2',4'-dimethoxyphenylaminomethyl) phenoxy radical of the carrier and in the following cycles the α-amino group of the amino acid added last, which is employed as the α-N-fmoc derivative, optionally with protected side chains, and which is activated by diisopropylcarbodiimide. Unreacted amino acids are washed off with dimethylformamide. The fmoc group is then removed by treating with 20% (v/v) piperidine in dimethylformamide. The other protective groups in this reaction remain unchanged. With removal of the α-N-protective group the next reaction cycle can begin. After the last amino acid corresponding to the given sequence has been added, the protective groups of the side chains and the bond to the carrier resin are cleaved by acidic hydrolysis by means of trifluoroacetic acid. The peptide is then purified by high-pressure liquid chromatography.

The other peptides having the sequences according to the invention are also synthesized according to the procedure described above. For comparison purposes, the following peptide, whose sequence is also derived from the PagC sequence, is additionally prepared:

Val Gly Tyr Glu Gly Ser Asn Ile Ser Ser Thr Lys Ile Asn  II (SEQ ID NO:7)

Example 2

Conjugation of the peptide CysGluHisSerThrGlnAspGlyAspSerPheSerAsnLys (SEQ ID NO:6) to glucose dehydrogenase a) Derivatization of the glucose dehydrogenase 30 mg of glucose dehydrogenase from Bacillus megaterium (Merck, Item No. 13732) are dissolved in 4 ml of sodium phosphate buffer (50 mM; pH 8.0). 6.78 mg of N-γ-maleimidobutyryloxysuccinimide (Calbiochem) dissolved in 50 μl of dimethyl sulphoxide are added to 2.4 ml of this solution and it is allowed to stand at room temperature for 30 minutes. The excess N-γ-maleimidobutyryloxysuccinimide is then removed chromatographically by gel filtration on PD10 columns (Pharmacia). After chromatography, 3.5 ml of solution of the activated carrier protein having a concentration of 4.5 mg/ml are obtained.

b) Coupling to the peptide 5.2 mg of the peptide, prepared according to Example 1, dissolved in 1 ml of sodium phosphate buffer (50 mM; pH 8.0) are added to 1.1 ml of the solution from the above step and the mixture is stirred at room temperature for 3 hours. The unbound peptide is then removed chromatographically by gel filtration on PD10 columns. After chromatography, 3.5 ml of solution of the conjugate having a concentration of 2.3 mg/ml are obtained.

Conjugates containing the other peptides mentioned in Example 1 are also prepared according to the procedure described above.

Example 3

Production of polyclonal antibodies against the peptide CysGluHisSerThrGlnAspGlyAspSerPheSerAsnLys (SEQ ID NO:6)

Two mice are in each case injected s.c. with an emulsion of 0.1 ml of conjugate from Example 2 and 0.1 ml of oil adjuvant (MISA 50, Seppic, FR). Three, five and seven weeks after the first injection, booster injections of the same amount follow. One week after the last injection, the animals are sacrificed and exsanguinated. After the blood has clotted, antiserum is obtained by centrifugation and sodium azide is added up to a final concentration of 0.02%. The antiserum is stored frozen at −20° C.

The other peptide conjugates produced according to Example 2 are also used for immunization according to the procedure described above.

Example 4

Production of monoclonal antibodies against the peptide CysGluHisSerThrGlnAspGlyAspSerPheSerAsnLys (SEQ ID NO:6)

Two mice are in each case injected s.c. with an emulsion of 0.1 ml of conjugate from Example 2 and 0.1 ml of oil adjuvant (MISA 50, Seppic, FR). Two, four and six weeks after the first injection, booster injections of the same amount follow. Three days after the last injection the animals are sacrificed and the spleen is isolated. The cells from the spleen are isolated according to customary methods and fused with a permanent murine cell line. From the fusion products, cell lines are selected which form antibodies against the peptide CysGluHisSerThrGlnAspGlyAspSerPheSerAsnLys (SEQ ID NO:6). Cell lines are screened using an ELISA-protocol. The respective peptide is conjugated to ovalbumin and coated on to a micro-titer plate. A conjugate of anti-mouse antibody containing alkaline phosphatase is used to detect bound antibody and identify expressing clones.

The other peptide conjugates produced according to Example 2 are also used for the production of monoclonal antibodies according to the procedure described above.

Example 5

Specific immunological detection of salmonellae a) Preculture of the enterobacteria Various enterobacteria to be analyzed are in each case inoculated into 10 ml of YT medium and incubated overnight at 37° C.

b) Pretreatment of the salmonellae for an SDS extraction of the external membrane proteins 2 ml are removed from each culture. The bacterial cells are removed by centrifugation (13,000 rpm, 5 min), resuspended in 2 ml of tris-buffered saline (TBS: 10 mM tris HCL pH 7.5; 0.9% NaCl) and removed by centrifugation again. For the extraction of external membrane proteins, the bacterial pellet is then resuspended in 2 ml of TBS which contains 0.025% of sodium dodecyl sulphate (SDS) and incubated for 45 minutes. After centrifugation for 10 minutes, 1.8 ml of supernatant are transferred to a new reaction vessel and the proteins contained in the extract are precipitated on ice by addition of trichloroacetic acid (10% final concentration) for 1.5 hours. After centrifugation for 1 5 minutes, the precipitate is washed in 500 μl of acetone, centrifuged for 10 minutes and, after removing the acetone, briefly air-dried. The precipitate is then dissolved in Lämmli sample buffer, treated with 1 μl of 2 N NaOH, and heated at 95° C. for 5 minutes.

c) Pretreatment of the enterobacteria for a cell fractionation 0.5 ml is taken from the overnight culture, diluted 1:25 with YT medium, and cultured up to an optical density, measured at 600 nm, of 0.7 at 37° C. The bacterial suspension is brought to a pH of 4.8 with 0.5 M sodium citrate and incubated for a further 2 hours. The cells are disrupted according to the method of Neu and Heppel (1965. J. Bacteriol. 240: 3685–3692) by freezing and thawing twice and subsequent ultrasonic treatment (4×30 seconds). The membrane fraction is recovered by sedimentation in an ultracentrifuge for 30 minutes at 100,000×g. The sedimented proteins are dissolved in Lämmli sample buffer (1.52 g of tris; 20 ml of glycerol; 2 g of SDS; 2 ml of 2-mercaptoethanol; 1 mg of Bromo-phenol Blue; to 100 ml with $H_2O$; pH 6.8 with HCl and NaOH and denatured at 95° C. for five minutes. The proteins are then separated at 150 volts by means of a discontinuous SDS-polyacrylamide gel electrophoresis (combined resolving and stacking gel). Composition of the resolving gel: 11.25 ml of tris HCL pH 8.8; 5.46 ml of $H_2O$; 12.45 ml of 30% acrylamide/0.8% bisacrylamide; 0.3 ml of 10% SDS; 0.36 ml of ammonium peroxodisulphate (32 mg/ml); 30 μl of TEMED (N,N,N',N'-tetramethyl-ethylenediamine). Stacking gel: 2.5 ml of tris HCL pH 6.8; 14.7 ml of $H_2O$; 2 ml of acrylamide/0.8% bisacrylamide; 0.2 ml of SDS; 0.4 ml of ammonium peroxodisulphate (32 mg/ml); 20 μl of TEMED.

The proteins separated in the gel are then transferred from the gel to a nitrocellulose membrane (HYBOND-C®; Amersham) by a semi-dry electroblotting method in a graphite chamber (Kyhse-Andersen. 1984. *J. Biochem. Biophys. Methods* 10: 203–209).

To block free protein binding sites, the nitrocellulose membrane containing the transferred proteins is boiled for an hour in a solution consisting of bovine serum albumin (BSA; 10 g/l) in phosphate-buffered saline (PBS). The antiserum obtained in Example 3 is diluted (1:250, if not stated otherwise) in PBS/BSA (10 g/l)/Polysorbate 20 (TWEEN® 20; ICI America; 0.5 g/l) and incubated at room temperature for an hour with the treated membrane. After washing the membrane three times in PBS/Polysorbate 20 (0.5 g/l), the membrane is incubated at room temperature for an hour with a peroxidase-labelled anti-mouse antibody which has previously been diluted 1:750 in the same dilution buffer. After washing twice in PBS/Polysorbate 20 (0.5 g/l) and washing once in tris-buffered saline (TBS), the substrate solution (4-chloro-1-napththol: 3 mg/ml in methanol +5 volumes of TBS+hydrogen peroxide–final concentration 0.1 g/l) is added thereto. The color reaction on the membrane (formation of a blue-black coloration) shows the reactivity of the antiserum with the proteins.

Results of the Immunoblots

Figure 1A:
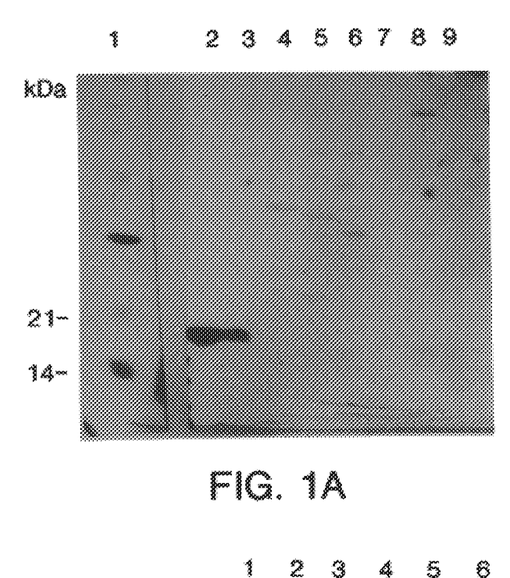
FIG. 1A and B shows immunoblots of antisera prepared against peptides according to the present invention.
Figure 1B:
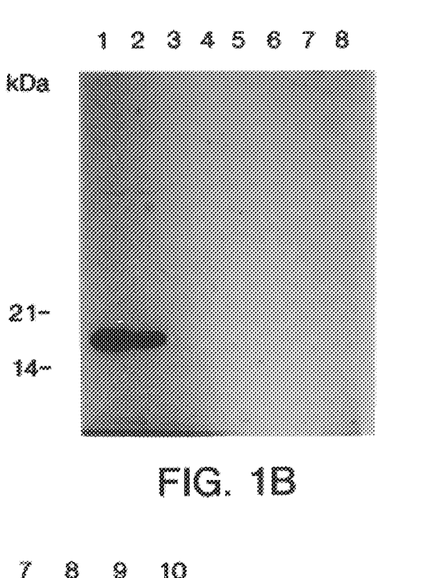

Immunoblots are carried out as described above using the peptide antisera produced according to Example 3 FIG. 1A and B shows immunoblots of the antisera (diluted 1:500) against peptide Id (SEQ ID NO:4) (A) and Ie (SEQ ID NO:5) (B) with protein preparations of various enterobacteria. Both analyzed Salmonella isolates S. typhimurium and S. choleraesuis, which are very divergent phylogenetically within the genus Salmonella, can be detected specifically by means of the reactivity of the antibodies produced against PagC from Salmonella. The Enterobacteriaceae investigated were specifically:

| Number | Blot A | Blot B |
| --- | --- | --- |
| 1 | Molecular weight standard | Salmonella typhimurium |
| 2 | Salmonella typhimurium | Salmonella choleraesuis |
| 3 | Salmonella choleraesuis | Yersinia enterolytica |
| 4 | Yersinia enterolytica | Enterobacter cloacae |
| 5 | Enterobacter cloacae | Escherichia coli |
| 6 | Escherichia coli | Shigella flexneri |
| 7 | Shigella flexneri | Citrobacter diversus |
| 8 | Citrobacter diversus | Proteus mirabilis |
| 9 | Proteus mirabilis | |

Figure 2:
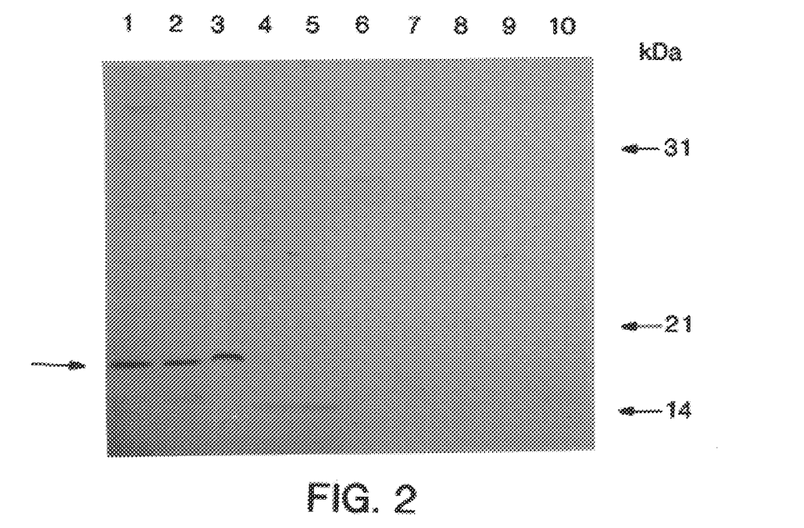
FIG. 2 shows the analysis of membrane fractions of various enterobacteria using an antiserum against peptide Ia (SEQ ID NO:1) in the immunoblot (dilution 1:200)

The PagC protein of the three Salmonella isolates S. typhimurium (1), S. enteritidis (2) and S. typhi(3) analyzed is clearly identifiable in the molecular weight range at 18 kD. The other bacteria investigated were: E. coli 5K (4), E. coli (5), C. diversus (6), Enterobacter cloacae (7), Shigella flexneri (8), Y. enterolytica (9) and Bordetella bronchoseptica (10); in all these cases no reaction was observed (see FIG. 2).

Figure 3A:
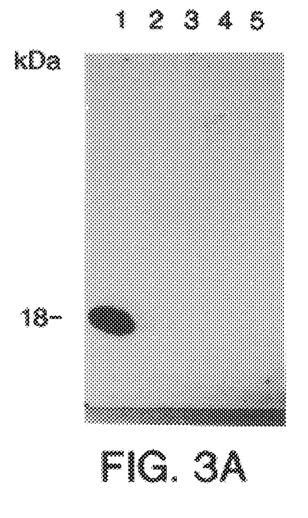
FIG. 3A–C shows the analysis of SDS-extracted proteins in the immunoblot (dilution 1:750)
Figure 3B:
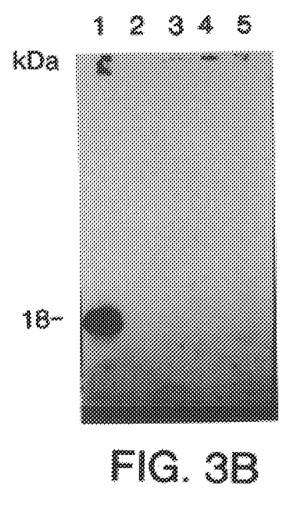
Figure 3C:
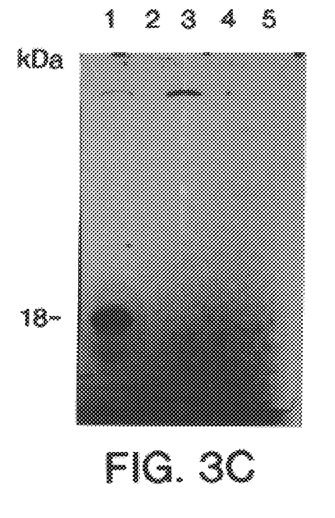

In this case, antisera against peptide Ia (SEQ ID NO:1) (A), peptide Ib (SEQ ID NO:2) (B) and peptide Ic (SEQ ID NO:3) (C) were reacted with SDS-extracted proteins from various enterobacteria (FIG. 3A–C). The bacteria investigated were specifically: S. typhimurium (1), E. coli (2), C. diversus (3), Y. enterolytica (4) and Enterobacter cloacae (5).

Comparison Example A

Non-specific detection of PagC using polyclonal antibodies against PagC

Figure 4:
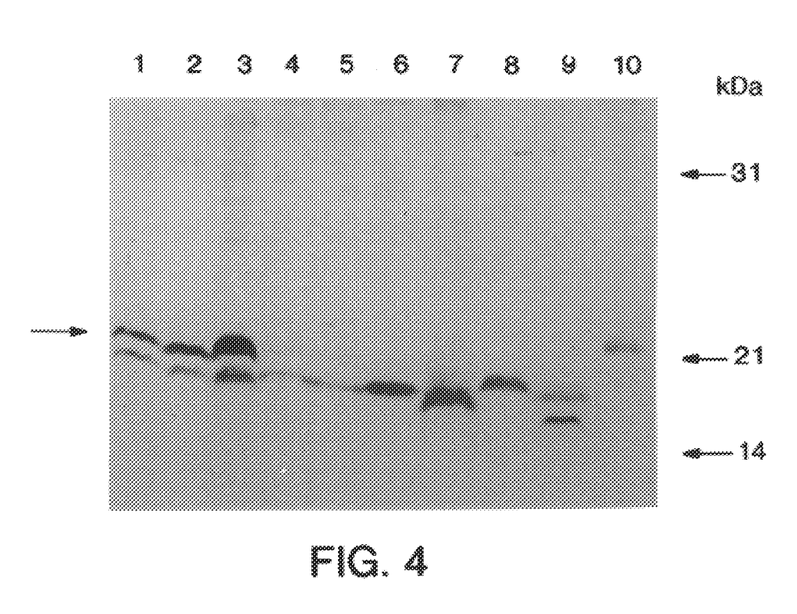
FIG. 4 shows non-specific detection of PagC using polyclonal antibodies against PagC. See Comparison Example A.

Protein pagC was cloned in Escherichia coli. Polyclonal antibodies against this protein were raised in rabbits using standard protocols. Anti-bodies against recombinant PagC protein (total molecule) are incubated with isolated proteins from various bacteria (Example 5) on nitrocellulose membranes. The bacteria investigated were specifically: S,typhimurium (1), S. enteritidis (2), S. typhi(3), E. coli 5K (4), E. coli (5), C. diversus (6), Enterobacter cloacae (7), Shigella flexneri (8), Y. enterolytica (9) and Bordetella bronchoseptica (10). As the stains in the molecular weight range 16–20 kilodaltons in FIG. 4 confirm, these antibodies also recognize the PagC-homologous proteins from Enterobacter cloacae and Yersinia enterocolitica or other hitherto uncharacterized proteins from other enterobacteria and are therefore unsuitable for a specific immunological detection of salmonellae.

Comparison Example B

Reaction of antibodies against a further peptide selected from the PagC sequence The antiserum against the peptide Val Gly Tyr Glu Gly Ser Asn Ile Ser Ser Thr Lys Ile Asn        II (SEQ ID NO:7)

which was selected from the PagC sequence like the peptides of formula Ia–Ie (SEQ ID NO:1 to SEQ ID NO:5), showed no reactivity with the PagC protein from Salmonella.

Example of Salmonellae Strains

Additional strains of Salmonella have been tested using antigenic peptides according to the present invention:

S. typhimurium

S. bredeney

S. arizonae

S. dublin

S. eimsbüttel

S. münchen

S. derby

S. hoograven

S. quinhon

S. enteritidis

S. typhi

S. newport

S. tallahasse

S. hadar

S. virchow

S. düsseldorf

S. mbandaka

S. waynr

S. pullorum

S. weslaco

S. chloerasuis

S. panama

S. takoradi

S. chester

S. anatum

S. saintpaul

All strains reacted positive with the antibody, whereas the reaction with controls (Escherichia col, Enterobacter cloacae, Proteus mirabilis and Citrobacter freundii) was negative. The antibodies were prepared essentially as described in Example 4 using peptide Ia (SEQ ID NO:1) as an immunogen; the peptide was linked to glucose dehydrogenase via a cysteic residue.

What is claimed is:

1. An isolated antibody which is specifically directed to an epitope of a peptide from protein PagC, said peptide having an amino acid sequence selected from the group consisting of:

Glu Pro Glu Gly Ile His Tyr His Asp Lys Phe Glu Val (SEQ ID NO:1) Ia;

Ala Thr Phe Lys Glu His Ser Thr Gln Asp Gly Asp Ser (SEQ ID NO: 2) Ib;

Gly Asp Arg Ala Ser Gly Ser Val Glu Pro Glu Gly (SEQ ID NO: 3) Ic;

Gln Ser Lys Val Gln Asp Phe Lys Asn Ile Arg (SEQ ID NO: 4) Id; and

Glu His Ser Thr Gln Asp Gly Asp Ser Phe Ser Asn Lys (SEQ ID NO: 5) Ie, wherein said antibody specifically detects Salmonella bacteria, but not *Escherichia coli, Citrobacter diversus, Yersinia enterolytica,* and *Enterobacter cloacae.*

2. An antibody conjugate comprising the antibody according to claim 1 conjugated to a detectable label.

3. The antibody conjugate according to claim 3, wherein the detectable label is an enzyme.

4. The antibody conjugate according to claim 3, wherein the enzyme is horseradish peroxidase or alkaline phosphatase.

5. A process for the immunological detection of a bacteria of the genus Salmonella comprising:

incubating a sample containing a Salmonella bacteria with the antibody according to claim 1;

detecting the binding of the antibody to the sample; and correlating the amount of binding with the presence of absence of the Salmonella bacteria.

6. A kit comprising the antibody according to claim 1 and a substrate solution for detecting an enzyme, wherein the enzyme is conjugated to said antibody or to a second antibody and the second antibody reacts with the antibody of claim 1.

7. The isolated antibody of claim 1, said peptide having the amino acid sequence Gly Asp Arg Ala Ser Gly Ser Val Glu Pro Glu Gly (SEQ ID NO: 3) Ic.

8. The isolated antibody of claim 1, said peptide having the amino acid sequence selected from the group consisting of:

Glu Pro Glu Gly Ile His Tyr His Asp Lys Phe Glu Val (SEQ ID NO: 1) Ia,

Ala Thr Phe Lys Glu His Ser Thr Gln Asp Gly Asp Ser (SEQ ID NO: 2) Ib;

Gln Ser Lys Val Gln Asp Phe Lys Asn Ile Arg (SEQ ID NO: 4) Id; and

Glu His Ser Thr Gln Asp Gly Asp Ser Phe Ser Asn Lys (SEQ ID NO: 5) Ie.

9. The isolated antibody of claim 1, wherein said antibody is specifically directed to an epitope of a peptide Id or Ie and wherein the antibody does not detect Shigella flexneri and Proteus mirabilis.

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: linear     ( i i ) MOLECULE TYPE: peptide     ( i i i ) HYPOTHETICAL: NO     ( i v ) ANTI-SENSE: NO     ( v i ) ORIGINAL SOURCE:
        ( A ) ORGANISM: Salmonella     ( x i ) SEQUENCE DESCRIPTION: SEQ ID NO: 1:

Glu Pro Glu Gly Ile His Tyr His Asp Lys Phe Glu Val
    1                    5                        10

( 2 ) INFORMATION FOR SEQ ID NO: 2:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: linear     ( i i ) MOLECULE TYPE: peptide     ( i i i ) HYPOTHETICAL: NO     ( i v ) ANTI-SENSE: NO     ( v i ) ORIGINAL SOURCE:
        ( A ) ORGANISM: Salmonella     ( x i ) SEQUENCE DESCRIPTION: SEQ ID NO: 2:

Ala Thr Phe Lys Glu His Ser Thr Gln Asp Gly Asp Ser
    1                    5                        10

( 2 ) INFORMATION FOR SEQ ID NO: 3:

( i ) SEQUENCE CHARACTERISTICS:
        ( A ) LENGTH: 12 amino acids
        ( B ) TYPE: amino acid
        ( C ) STRANDEDNESS: unknown
        ( D ) TOPOLOGY: linear     ( i i ) MOLECULE TYPE: peptide     ( i i i ) HYPOTHETICAL: NO     ( i v ) ANTI-SENSE: NO     ( v i ) ORIGINAL SOURCE:
        ( A ) ORGANISM: Salmonella     ( x i ) SEQUENCE DESCRIPTION: SEQ ID NO: 3:

Gly Asp Arg Ala Ser Gly Ser Val Glu Pro Glu Gly
    1                    5                        10

( 2 ) INFORMATION FOR SEQ ID NO: 4:

( i ) SEQUENCE CHARACTERISTICS:

(A) LENGTH: 11 amino acids
(B) TYPE: amino acid
(C) STRANDEDNESS: unknown
(D) TOPOLOGY: linear (ii) MOLECULE TYPE: peptide (iii) HYPOTHETICAL: NO (iv) ANTI-SENSE: NO (vi) ORIGINAL SOURCE:
(A) ORGANISM: Salmonella (xi) SEQUENCE DESCRIPTION: SEQ ID NO: 4:

Gln Ser Lys Val Gln Asp Phe Lys Asn Ile Arg
1               5                   10

(2) INFORMATION FOR SEQ ID NO: 5:

(i) SEQUENCE CHARACTERISTICS:
(A) LENGTH: 13 amino acids
(B) TYPE: amino acid
(C) STRANDEDNESS: unknown
(D) TOPOLOGY: linear (ii) MOLECULE TYPE: peptide (iii) HYPOTHETICAL: NO (iv) ANTI-SENSE: NO (vi) ORIGINAL SOURCE:
(A) ORGANISM: Salmonella (xi) SEQUENCE DESCRIPTION: SEQ ID NO: 5:

Glu His Ser Thr Gln Asp Gly Asp Ser Phe Ser Asn Lys
1               5                   10

(2) INFORMATION FOR SEQ ID NO: 6:

(i) SEQUENCE CHARACTERISTICS:
(A) LENGTH: 14 amino acids
(B) TYPE: amino acid
(C) STRANDEDNESS: unknown
(D) TOPOLOGY: linear (ii) MOLECULE TYPE: peptide (iii) HYPOTHETICAL: NO (iv) ANTI-SENSE: NO (vi) ORIGINAL SOURCE:
(A) ORGANISM: Salmonella (xi) SEQUENCE DESCRIPTION: SEQ ID NO: 6:

Cys Glu His Ser Thr Gln Asp Gly Asp Ser Phe Ser Asn Lys
1               5                   10

(2) INFORMATION FOR SEQ ID NO: 7:

(i) SEQUENCE CHARACTERISTICS:
(A) LENGTH: 14 amino acids
(B) TYPE: amino acid
(C) STRANDEDNESS: unknown
(D) TOPOLOGY: linear (ii) MOLECULE TYPE: peptide (iii) HYPOTHETICAL: NO (iv) ANTI-SENSE: NO (v i) ORIGINAL SOURCE:
    (A) ORGANISM: Salmonella (x i) SEQUENCE DESCRIPTION: SEQ ID NO: 7:

Val Gly Tyr Glu Gly Ser Asn Ile Ser Ser Thr Lys Ile Asn
 1           5                   10

(2) INFORMATION FOR SEQ ID NO: 8:

(i) SEQUENCE CHARACTERISTICS:
        (A) LENGTH: 14 amino acids
        (B) TYPE: amino acid
        (C) STRANDEDNESS: unknown
        (D) TOPOLOGY: linear (ii) MOLECULE TYPE: peptide (iii) HYPOTHETICAL: NO (iv) ANTI-SENSE: NO (v i) ORIGINAL SOURCE:
        (A) ORGANISM: Salmonella (x i) SEQUENCE DESCRIPTION: SEQ ID NO: 8:

Arg Gly Val Asn Val Lys Tyr Arg Tyr Glu Asp Asp Ser Phe
 1           5                   10